(12) United States Patent
Zhong et al.

(10) Patent No.: US 8,163,326 B2
(45) Date of Patent: Apr. 24, 2012

(54) IMPLANTABLE OR INSERTABLE MEDICAL DEVICES VISIBLE UNDER MAGNETIC RESONANCE IMAGING

(75) Inventors: Sheng-Ping Zhong, Northborough, MA (US); Ronald A. Sahatjian, Lexington, MA (US); Enxin Ma, Natick, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 527 days.

(21) Appl. No.: 11/637,263

(22) Filed: Dec. 12, 2006

(65) Prior Publication Data

US 2007/0167735 A1 Jul. 19, 2007

Related U.S. Application Data

(63) Continuation of application No. 09/993,907, filed on Nov. 27, 2001, now abandoned.

(51) Int. Cl.
*B05D 3/02* (2006.01)
*B05D 3/06* (2006.01)
*A61B 5/05* (2006.01)

(52) U.S. Cl. ....... 427/2.1; 427/2.24; 427/2.25; 600/410; 600/420

(58) Field of Classification Search ........... 427/2.1–2.31
See application file for complete search history.

(56) References Cited

U.S. PATENT DOCUMENTS

| | | | |
|---|---|---|---|
| 4,593,053 A | 6/1986 | Jevne et al. | 523/111 |
| 4,729,892 A * | 3/1988 | Beall | 424/9.3 |
| 4,985,233 A | 1/1991 | Klaveness et al. | 424/9 |
| 4,989,608 A | 2/1991 | Ratner | 128/653 |
| 5,122,363 A | 6/1992 | Balkus, Jr. et al. | 424/9 |
| 5,154,179 A | 10/1992 | Ratner | 128/653.4 |
| 5,304,121 A | 4/1994 | Sahatjian | 604/53 |
| 5,331,027 A | 7/1994 | Whitbourne | 524/37 |
| 5,336,208 A | 8/1994 | Rosenbluth et al. | 604/329 |
| 5,352,431 A | 10/1994 | Hashiguchi et al. | 424/4 |
| 5,514,379 A * | 5/1996 | Weissleder et al. | 424/426 |
| 5,562,099 A | 10/1996 | Cohen et al. | 128/662.02 |
| 5,681,544 A | 10/1997 | Schmitt-Willich et al. | 424/9.34 |
| 5,693,034 A | 12/1997 | Buscemi et al. | 604/265 |
| 5,702,672 A | 12/1997 | Thompson | 424/9.42 |
| 5,702,754 A | 12/1997 | Zhong et al. | 427/2.12 |
| 5,728,079 A | 3/1998 | Zhong et al. | 604/280 |
| 5,744,958 A | 4/1998 | Werne | 324/318 |
| 5,788,687 A | 8/1998 | Batich et al. | 604/890 |
| 5,788,979 A | 8/1998 | Alt et al. | 424/426 |
| 5,817,017 A * | 10/1998 | Young et al. | 600/433 |
| 5,817,292 A | 10/1998 | Snow et al. | 600/433 |
| 5,869,129 A | 2/1999 | Aben et al. | 427/64 |
| 6,026,316 A | 2/2000 | Kucharczyk et al. | 600/420 |
| 6,060,534 A | 5/2000 | Ronan et al. | 523/113 |
| 6,096,018 A | 8/2000 | Luzio et al. | 604/500 |
| 6,096,021 A | 8/2000 | Helm et al. | 604/509 |
| 6,112,908 A * | 9/2000 | Michaels | 210/506 |
| 6,123,920 A | 9/2000 | Gunther et al. | 424/9.322 |
| 6,176,849 B1 | 1/2001 | Yang et al. | 604/265 |
| 6,184,266 B1 | 2/2001 | Ronan et al. | 523/113 |
| 6,207,134 B1 | 3/2001 | Fahlvik et al. | 424/9.322 |
| 6,238,340 B1 | 5/2001 | Alt et al. | 600/431 |
| 6,261,630 B1 | 7/2001 | Nazarova et al. | 427/2.12 |
| 6,270,748 B1 | 8/2001 | Annan et al. | |
| 6,272,370 B1 | 8/2001 | Gillies et al. | 600/411 |
| 6,294,152 B1 | 9/2001 | Davies et al. | 424/9.361 |
| 6,316,522 B1 | 11/2001 | Loomis et al. | 523/105 |
| 6,463,317 B1 | 10/2002 | Kucharczyk et al. | 600/411 |
| 6,475,516 B2 | 11/2002 | DiCosmo et al. | 424/450 |
| 6,610,269 B1 * | 8/2003 | Klaveness et al. | 424/9.1 |
| 6,794,458 B2 * | 9/2004 | Haddad et al. | 525/326.7 |
| 2002/0061871 A1 * | 5/2002 | Peng et al. | 514/185 |
| 2003/0023190 A1 | 1/2003 | Cox | 600/585 |
| 2003/0099764 A1 | 5/2003 | Li et al. | 427/2.24 |
| 2003/0100830 A1 | 5/2003 | Zhong et al. | 600/431 |
| 2003/0170308 A1 * | 9/2003 | Cleary et al. | 424/486 |
| 2004/0143180 A1 | 7/2004 | Zhong et al. | |
| 2004/0249333 A1 | 12/2004 | Bergheim et al. | 604/8 |

FOREIGN PATENT DOCUMENTS

| | | |
|---|---|---|
| EP | 0 702 976 A1 | 3/1996 |
| EP | 0 775 500 A1 | 11/1996 |
| EP | 0 963 796 A2 | 12/1999 |
| JP | J01113059 | 5/1989 |
| WO | 9310440 | 5/1993 |
| WO | WO 94/08629 | 4/1994 |
| WO | WO 94/23782 | 10/1994 |
| WO | WO 99/60920 | 12/1999 |
| WO | WO 00/50103 A1 | 8/2000 |
| WO | WO 01/81460 A1 | 11/2001 |
| WO | WO 02/22186 A1 | 3/2002 |
| WO | WO 03/045457 A2 | 6/2003 |
| WO | WO 03/094975 A1 | 11/2003 |

OTHER PUBLICATIONS

Xiqun Jiang et al., "Novel Magnetic Resonance Signal Enhancing Coating Material," *Advance Materials*, vol. 13, No. 7, Apr. 4, 2001, pp. 490-493. Abstract of JP10290839, Nov. 4, 1998.

* cited by examiner

*Primary Examiner* — Timothy Meeks
*Assistant Examiner* — Cachet Sellman
(74) *Attorney, Agent, or Firm* — Vidas, Arrett & Steinkraus, P.A.

(57) ABSTRACT

Disclosed is an implantable or insertable medical device comprising (a) a substrate and (b) a hydrogel polymer coating at a least a portion of the surface of the substrate, wherein the hydrogel polymer is adapted to render the medical device visible under magnetic resonance imaging (MRI) upon insertion or implantation of the medical device into a patient. Also disclosed is the use of such a hydrogel coated implantable or insertable medical device in a medical procedure, wherein during or after insertion or implantation of the medical device in a patient, the position of the medical device is viewed under MRI. The use of a hydrogel polymer for coating a medical device wherein the hydrogel polymer is adapted to render a medical device coated with the hydrogel polymer visible under MRI and a hydrogel polymer adapted to render a medical device coated therewith visible under MRI are also disclosed.

33 Claims, No Drawings

IMPLANTABLE OR INSERTABLE MEDICAL DEVICES VISIBLE UNDER MAGNETIC RESONANCE IMAGING

STATEMENT OF RELATED APPLICATIONS

This application is a continuation of U.S. patent application Ser. No. 09/993,907, filed Nov. 27, 2001, now abandoned entitled "Implantable or Insertable Medical Devices Visible Under Magnetic Resonance Imaging." This application is also related to U.S. patent application Ser. No. 10/755,164, filed Jan. 9, 2004, entitled "Medical Devices Visible Under Magnetic Resonance Imaging." Both of the prior applications are incorporated herein by reference in their entireties.

FIELD OF THE INVENTION

The present invention relates to implantable or insertable medical devices adapted to be visible under magnetic resonance imaging (MRI). More particularly, the present invention relates to medical devices provided with a coating adapted to render the medical device visible under MRI; the use of such medical devices in a medical procedure during or after which the position of the medical device is viewed by MRI; and, the use of coatings adapted to render medical devices coated therewith visible under MRI.

BACKGROUND OF THE INVENTION

The ability to non-invasively image internal body structures and diseased tissues within a patient's body is an extremely important diagnostic tool in the practice of modern medicine. Among such non-invasive imaging techniques include magnetic resonance imaging (MRI), x-ray imaging, ultrasonic imaging, x-ray computed tomography, emission tomography, and others. Magnetic resonance imaging can provide two-dimensional cross-sectional images through a patient, providing color or gray scale contrast images of a portion of the body. These two-dimensional images can then be reconstructed to provide a 3-dimensional image of a portion of the body. MRI is advantageous, inter alia, because it does not expose the patient or medical practitioner to harmful radiation and can provide detailed images of the observed area. These detailed images are valuable diagnostic aids to medical practitioners and can be used to devise, monitor or alter a treatment approach.

Magnetic resonance imaging (MRI) produces images by differentiating detectable magnetic species in the portion of the body being imaged. In the case of $^1$H MRI, the detectable species are protons (hydrogen nuclei) that possess an inherent spin magnetic moment such that these protons behave like tiny magnets. Images are obtained by placing the patient or area of interest within a powerful, highly uniform, static magnetic field. The protons in the area of interest align like tiny magnets in this field. Radiofrequency pulses are then utilized to create an oscillating magnetic field perpendicular to the main field, from which the nuclei absorb energy and move out of alignment with the static field, in a state of excitation. As the nuclei return from excitation to the equilibrium or relaxed state, a signal induced in the receiver coil of the instrument by the nuclear magnetization can then be transformed by a series of algorithms into diagnostic images. Images based on different tissue characteristics can be obtained by varying the number and sequence of pulsed radiofrequency fields in order to take advantage of magnetic relaxation properties of the detectable protons in the area of interest.

The environment of the detectable protons alters the magnetic properties thereof such that different field strengths and pulsation frequencies affect the ability of the MRI device to detect such protons and differentiate them from other protons in the surrounding environment. In order to obtain good images, MRI relies upon the differentiation of such protons to provide contrast between the area of interest and the surrounding environment. For example, diseased or damaged tissue may result in a sufficiently different environment for the detectable protons therein relative to that of protons in the surrounding environment. Sufficient contrast is thereby provided by the inherently different environments to produce a good image of the area of interest.

However, in order to enhance the differentiation of detectable species in the area of interest from those in the surrounding environment, contrast agents are often employed. These agents alter the magnetic environment of the detectable protons in the area of interest relative to that of protons in the surrounding environment and, thereby, allow for enhanced contrast and better images of the area of interest.

Contrast agents thus function to alter the signal intensity arising from detectable protons from that arising from detectable protons in the surrounding environment, thereby differentiating the area of interest from the surrounding environment. Nearly all of the classes of contrast agents create their desired effect by changing the spin-lattice relaxation time ($T_1$) and/or the spin-spin relaxation time ($T_2$) of the detectable protons. Those contrast agents that operate predominantly on spin-spin relaxation times are the superparamagnets, such as particulate iron oxides. Those contrast agents that operate predominantly on the spin-lattice relaxation time are the paramagnets. These species possess unpaired electrons and thus have a net magnetic moment. It is the magnetic moment of the contrast agent that leads to an increase in the spin-lattice relaxation rate of detectable protons, thereby differentiating these protons from those in the surrounding environment. For contrast-enhanced MRI it is desirable that the contrast agent have a large magnetic moment, with a relatively long electronic relaxation time. Based upon these criteria, contrast agents such as Gd(III), Mn(II) and Fe(III) have been employed. Gadolinium(III) has the largest magnetic moment among these three and is, therefore, a widely-used paramagnetic species to enhance contrast in MRI. Chelates of paramagnetic ions such as Gd-DTPA (gadolinium ion chelated with the ligand diethylenetriaminepentaacetic acid) have been employed as MRI contrast agents. Chelation of the gadolinium or other paramagnetic ion is believed to reduce the toxicity of the paramagnetic metal by rendering it more biocompatible, and can assist in localizing the distribution of the contrast agent to the area of interest.

Implantable or insertable medical devices such as catheters, guidewires, balloons, stents, and a variety of other implantable or insertable medical devices are conventionally used to both diagnose and treat medical conditions. To maximize the effectiveness of such medical devices, it is commonly desirable to both properly position the device within a patient and thereafter ascertain the precise location of such device upon implantation or insertion thereof.

In recent years, there has been a trend to use MRI as a tracking/guiding tool for monitoring interventional procedures using an implantable or insertable medical device or as a tool to determine the position of the device upon implantation or insertion thereof. The ability of MI to produce extremely detailed images of an area of interest, and the minimization of harmful radiation exposure to the patient or medical practitioner of radiation attendant to the use of X-ray imaging, are distinct advantages of MRI over other imaging techniques. To this end, MRI has been used with varying degrees of success to assist in the placement of a medical device and/or to determine the position of a medical device upon insertion or implantation. Unfortunately, most implantable or insertable medical devices are composed of materials such as organic polymers, metals, ceramics, or composites thereof, which do not produce adequate signals for detection by MRI techniques. Therefore, the effectiveness of MRI to monitor the insertion of such devices and the position thereof after insertion or implantation has been limited.

It would, therefore, be desirable to provide implantable or insertable medical devices that are visible under MRI. For example, it has been proposed in U.S. Pat. No. 5,154,179 to incorporate MRI contrast enhancing agents such as ferromagnetic particles within the polymeric material used to construct catheters. This patent discloses incorporation of ferromagnetic particles such as iron and iron oxides during the extrusion of the plastic to form the catheter. The embedded ferromagnetic particles are disclosed to make the catheter visible under MRI by providing contrast with respect to the surrounding body tissues. The direct incorporation of ferromagnetic or paramagnetic materials into the polymeric material of catheters and other implantable or insertable medical devices, however, suffers from numerous drawbacks. For example, in order to provide enhanced contrast under MRI, paramagnetic materials, such as paramagnetic ions, require the proximity of water or another proton-bearing substance. It is difficult to incorporate such substances during the shaping of the polymeric materials used to construct the medical device. For example, water associated with hydrated paramagnetic ions can be readily lost during high temperature extrusion of the polymeric material used to construct the medical device. Moreover, the incorporation of such ferromagnetic or paramagnetic materials can detrimentally affect the requisite mechanical properties, such as strength and flexibility, of the polymeric materials used to construct the implantable or insertable medical device.

U.S. Pat. No. 5,154,179 also discloses introduction of a liquid or gel contrast agent containing a paramagnetic material into a catheter lumen. The paramagnetic material is disclosed to provide contrast with respect to surrounding body tissues to render the catheter visible under MRI. The incorporation of a liquid or gel in the catheter is difficult from a manufacturing view, limits the flexibility of the catheter, and is generally inconvenient.

U.S. Pat. No. 5,817,017 discloses the incorporation of paramagnetic ionic particles into non-metallic materials used to construct catheters and other medical devices to provide such devices with enhanced visibility under MRI. The paramagnetic ionic particles comprise paramagnetic ions incorporated with water or other proton-donating fluid into carrier particles such as zeolites, molecular sieves, clays, synthetic ion exchange resins and microcapsules. This patent discloses that the paramagnetic ionic particles can be combined with suitable polymeric materials and extruded into a desired shape, such as a flexible tube. This patent further discloses that extrusion of polymeric materials incorporating such paramagnetic ionic particles can be conducted without substantial loss of the proton-donating fluid, which is essential for image enhancement using the paramagnetic metals. Among paramagnetic ions that can be incorporated into the carrier particles are mentioned trivalent gadolinium. Among proton-donating fluids that can be incorporated with the paramagnetic ions in the carrier particles, are water, alcohols such as glycerols (e.g., propylene glycol, polyethylene glycol and ethylene glycol), detergents such as sulfonated compounds, ethers such as glyme and diglyme, amines, imidazoles, and Tris.

Despite these and other attempts to render implantable or insertable medical devices visible under MRI, there remains a need for a simplified, cost-effective approach that avoids the disadvantages of the methods discussed above.

The present invention is, therefore, directed to implantable or insertable medical devices adapted to be visible under magnetic resonance imaging (MRI). More particularly, the present invention is directed to medical devices provided with a coating adapted to render the medical device visible under MRI; the use of such medical devices in a medical procedure during or after which the position of the medical device can be viewed by MRI; and, the use of coatings adapted to render medical devices coated therewith visible under MRI.

SUMMARY OF THE INVENTION

In one embodiment, the present invention is directed to an implantable or insertable medical device comprising (a) a substrate; and (b) a hydrogel polymer coating at least a portion of the substrate surface, wherein the hydrogel polymer is adapted to render the medical device visible under magnetic resonance imaging upon insertion or implantation of the medical device into a patient.

In another embodiment, the present invention is directed to the use of an implantable or insertable medical device of the present invention in a medical procedure, wherein during or after insertion or implantation of the medical device in a patient, the position of the medical device is viewed under magnetic resonance imaging.

In still another embodiment, the present invention is directed to the use of a hydrogel polymer for coating at least a portion of the surface of a medical device, wherein the hydrogel polymer is adapted to render the medical device coated with the hydrogel polymer visible under magnetic resonance imaging during or after insertion or implantation of the medical device in a patient.

In a further embodiment, the present invention is directed to a hydrogel polymer adapted to render a medical device coated with the hydrogel polymer visible under magnetic resonance imaging during or after insertion of the medical device in a patient.

The hydrogel polymer may be adapted to render a medical device coated therewith visible under MRI by decreasing the relaxation time of detectable species associated with said hydrogel polymer relative to the relaxation time of detectable species in the environment surrounding the device. The detectable species may comprise, e.g., protons in water molecules or hydroxyl groups associated with the hydrogel polymer.

The hydrogel polymer may also be adapted by cross-linking the hydrogel polymer to a degree sufficient to render said medical device visible under magnetic resonance imaging upon insertion or implantation of said medical device into a patient.

The hydrogel polymer may also be adapted to render a medical device coated therewith visible under MRI by incorporating a member selected from the group consisting of paramagnetic ions, paramagnetic particles or paramagnetic ion chelation complexes in the hydrogel polymer. In some preferred embodiments, paramagnetic ions include materials such as gadolinium(III); paramagnetic particles include materials such as starch-coated iron oxide particles; and paramagnetic ion chelation complexes include materials such as gadolinium diethylenetriamine pentaacetic acid. The hydrogel polymer itself may also comprise paramagnetic ion chelating groups. In some preferred embodiments, the paramagnetic ion chelating groups include carboxyl groups and polyaminopolycarboxylic acid groups covalently bonded to the hydrogel polymer. Among some presently preferred hydrogel polymers are included polyacrylic acids and copolymers of acrylic acid and acrylamide, which may be cross-linked.

DETAILED DESCRIPTION OF THE INVENTION

It is known to provide implantable or insertable medical devices with a coating on a surface of the device. Such coatings may be provided for various purposes including, but not limited to, carrying a therapeutic agent for localized delivery to a target area within the body; providing a lubricious surface to facilitate introduction of the medical device into the patient during an interventional procedure; improving the biocompatibility of the medical device with the surrounding environment; or, for a combination of such or other purposes. Among coatings that have been proposed for implantable or insertable medical devices are polymeric materials such as hydrogels.

Hydrogels are typically hydrophilic polymeric materials that have the ability to absorb large amounts, up to many times the weight of the hydrogel itself, of water or other polar molecules. Hydrogels have been disclosed as coatings for implantable or insertable medical devices or as materials for constructing the device itself in, for example, U.S. Pat. Nos. 6,316,522; 6,261,630; 6,184,266; 6,176,849; 6,096,108; 6,060,534; 5,702,754; 5,693,034; and, 5,304,121, each of which is assigned to Boston Scientific Corporation or SciMed Life Systems, Inc. and is incorporated herein in its entirety by reference. Hydrogels, such as those described in the foregoing exemplary U.S. patents, can be based on synthetic or naturally occurring materials, or a composite thereof; can be biodegradable or substantially non-biodegradable; and, can be modified or derivatized in numerous ways to render the hydrogel more suitable for a desired purpose. For example, the hydrogel can be modified by chemically cross-linking with, for example, a polyfunctional cross-linking agent that is reactive with functional groups covalently bonded to the polymer structure. The hydrogel polymer can also be ionically cross-linked with, for example, polyvalent metal ions. Many hydrogel polymers mentioned herein can be both chemically and ionically cross-linked. Therefore, chemically and ionically cross-linkable hydrogel polymers are not necessarily mutually exclusive groups of hydrogel polymers.

Cross-linking of a hydrogel polymer can be advantageous, for example, to provide a more rigid material. Cross-linking may also be conducted, for example, to render the hydrogel less soluble in a particular environment or to modify the ability of the hydrogel polymer to absorb water or to modify the manner in which water or other molecules, compounds or groups are associated with the hydrogel polymer MRI based on detection of the spin relaxation of $^1$H nuclei (protons) relies on the differentiation of protons in the area of interest relative to those in the surrounding environment. For example, protons in water molecules in the area of interest, while detectable using MRI, are often not sufficiently differentiated from protons surrounding the area of interest to provide the contrast necessary for producing a good image using MRI. However, by changing the magnetic environment of the protons in the water molecules in the area of interest relative to that of protons in the surrounding environment, enhanced detection and contrast can be achieved. Among methods generally known for enhancing the contrast of protons in water molecules are included, as discussed above, decreasing the spin relaxation time of the protons by incorporating a paramagnetic species such as gadolinium(III) in the environment of the water molecules in the area of interest.

The present invention is based on the adaptation of hydrogel polymers to render an implantable or insertable medical device visible under MRI when the hydrogel polymer is provided as a coating on at least a portion of the surface of the implantable or insertable medical device. Hydrogel polymers are especially suitable for differentiating MRI detectable species, such as protons associated with the hydrogel polymer, from protons in the environment surrounding the device. Contrast, which is essential for detailed images using MRI, can thereby be achieved by adapting the hydrogel polymers such that detectable species associated with the hydrogel polymers are differentiated from detectable species in the environment surrounding the medical device coated with the hydrogel polymer.

Without being bound by theory, it is believed that hydrogel polymers are particularly suitable for use in the present invention because, inter alia, these polymers, provided as coatings on implantable or insertable medical devices, can be adapted to provide a magnetic environment for detectable species associated with the hydrogel polymer that differs from the magnetic environment of detectable species in the environment surrounding the coated device. The magnetic environment experienced by detectable species such as protons associated with the adapted hydrogel polymer coating is, thus, sufficiently different from the magnetic environment surrounding the medical device such that protons associated with the hydrogel polymer coating have enhanced detectability under MRI.

As used herein, the term "associated with" is meant to include various means by which the detectable species, such as protons, are incorporated within the hydrogel polymer, including but not limited to, ionic bonding, hydrogen bonding, covalent bonding, Van der Waals bonding, physical entrapment and combinations of the same. Thus, for example, detectable protons may be present in groups, such as pendant groups that are covalently or ionically bonded to the hydrogel polymer; or they may be present in molecules such as water or other molecules, compounds or groups that are absorbed within or adsorbed on the hydrogel polymer, or otherwise immobilized within the hydrogel polymer matrix. Immobilization of such detectable species may be facilitated by providing a cross-linked hydrogel polymer matrix. Such absorption, adsorption and/or cross-linking immobilization may be further facilitated by, for example, hydrogen bonding, ionic bonding or, more generally, electrostatic interaction of molecules, compounds or groups comprising the detectable species with the hydrogel polymer or groups covalently or ionically bonded to the hydrogel polymer.

Hydrogel polymers that can be adapted such that, when provided as a coating on the surface of an implantable or insertable medical device of the present invention, the medical device is rendered visible under MRI include, without limitation, any of the hydrogels disclosed in U.S. Pat. Nos. 6,316,522; 6,261,630; 6,184,266; 6,176,849; 6,096,108; 6,060,534; 5,702,754; 5,693,034; and, 5,304,121, mentioned above. Examples of hydrogel polymers that can be adapted to render a medical device visible under MRI include, without limitation, polyacrylates; poly(acrylic acid); poly(methacrylic acid); polyacrylamides; poly(N-alkylacrylamides); polyalkylene oxides; poly(ethylene oxide); poly(propylene) oxide; poly(vinyl alcohol); polyvinyl aromatics; poly(vinylpyrrolidone); poly(ethyleneimine); polyethylene amine; polyacrylonitrile; polyvinyl sulfonic acid; polyamides; poly (L-lysine); hydrophilic polyurethanes; maleic anhydride polymers; proteins; collagen; cellulosic polymers; methyl cellulose; carboxymethyl cellulose; dextran; carboxymethyl dextran; modified dextran; alginates; alginic acid; pectinic acid; hyaluronic acid; chitin; pullulan; gelatin; gellan; xanthan; carboxymethyl starch; chondroitin sulfate; guar; starch; and copolymers, mixtures and derivatives thereof.

Hydrogel polymers are hydrophilic and can absorb, relative to their weight, relatively large amounts of water, typically from about 30 wt % to about 50 wt % or more, or other polar molecules. Thus, when provided as a coating on a substrate such as the surface of a medical device, the hydrogel polymer can swell, upon absorption of water, to several times its thickness in the absence of the absorbed water. Water, as discussed above, comprises protons that are detectable using MRI. It has been discovered that hydrogel polymers can be adapted such that water molecules or other detectable species associated with the hydrogel polymer experience a substantially different magnetic environment relative to detectable species in the surrounding environment. Therefore, when such hydrogel polymer is provided as a coating on an implantable or insertable medical device, enhanced detection of protons in water molecules associated with the hydrogel coating is observed, rendering the medical device visible under MRI.

While not wishing to be bound by theory, the enhanced ability to detect protons in water or other molecules, compounds or groups associated with the hydrogel polymer may result from decreasing the spin relaxation time of the protons in the water, other molecules, compounds or groups associated with the hydrogel coating.

Molecules other than water, or in addition to water, may also be associated with the hydrogel polymer to adapt the hydrogel polymer to render the medical device coated therewith visible under MRI. Such molecules are those that can be associated with the hydrogel polymer and comprise species, such as protons, that are detectable using MRI when incorporated within the hydrogel polymer. Among such molecules are included, but not limited to, hydroxyl-group containing compounds such as alkanols, e.g., ethanol, glycerine (glycerol), ethylene glycol, propylene glycol, polyethylene glycol, polypropylene glycol and other hydroxylated and polyhydroxylated compounds that are known in art and are substantially non-toxic. When such hydroxyl-group containing compounds are associated with the hydrogel polymer, the protons in the hydroxyl groups may be sufficiently differentiated from protons in the environment surrounding the implantable or insertable medical device such that the device coated with the hydrogel polymer incorporating such compounds is rendered visible under MRI.

The detectable species associated with the hydrogel polymer may be present in a compound, such as water or other hydroxylated molecule, which is dispersed or absorbed within the hydrogel polymer matrix and/or adsorbed on a surface thereof. For example, such compounds may be associated with the hydrogel polymer by a mechanism such as hydrogen bonding. However, it is understood that the hydrogel polymer may also be adapted such that the detectable species are present in groups that are chemically bonded, e.g., by covalent or ionic bonding, to the polymer itself. Thus, the compound comprising the detectable species may be covalently bonded to a functional group that is itself covalently bonded to the hydrogel polymer. Binding of the compound comprising the detectable species may thus result from, e.g., reaction of a hydroxyl group inherently found in the compound with a functional group in the hydrogel polymer. The compound containing the detectable species may also be modified from its inherent state to contain one or more groups reactive with a functional group in the hydrogel polymer to form, e.g., an amide, ester or other linkage of the compound to the hydrogel polymer.

The hydrogel polymer of the present invention may be cross-linked. Cross-linked hydrogel polymers, when coated on an implantable or insertable medical device, are particularly advantageous for use in rendering the medical device visible under MRI upon insertion or implantation of the device. In accordance with this embodiment of the present invention, hydrogel polymers may be adapted by cross-linking to a degree sufficient to render the medical device visible under magnetic resonance imaging upon insertion or implantation of the medical device into a patient. It is believed that by varying the degree of cross-linking, the magnetic environment experienced by detectable species such as protons in water or other molecules, compounds or groups associated with the hydrogel polymer may be modified, relative to the magnetic environment surrounding the medical device, thereby resulting in enhanced visibility under MRI of such detectable species associated with the hydrogel polymer coating. The enhanced visibility of the detectable species in the cross-linked hydrogel polymer coating renders the medical device visible under MRI upon insertion or implantation of the coated medical device into a patient.

As discussed more fully below, cross-linked hydrogels are also particularly advantageous to incorporate, within the cross-linked hydrogel, paramagnetic materials such as paramagnetic ions, paramagnetic ion chelation complexes, paramagnetic particles and other materials that enhance the visibility under MRI of detectable species such as protons in water or other molecules, compounds or groups associated with the hydrogel polymer. Such paramagnetic materials generally function by reducing the spin relaxation time of such detectable species, thereby differentiating such species from detectable species in the environment surrounding the implantable or insertable medical device and, consequently, providing the detectable species associated with the hydrogel polymer with enhanced visibility under MRI.

Among cross-linked hydrogel polymers useful in the present invention are those disclosed in U.S. Pat. No. 5,702,754 to Zhong et al. Such polymers are characterized by the presence therein of organic acid functional groups that are reactive with polyfunctional cross-linking agents. By "organic acid functional group" is meant any organic group containing an acidic hydrogen atom such as a carboxylic, sulfonic or phosphoric acid group or a metal salt of any such acid group, particularly alkali metal salts such as lithium, sodium and potassium salts, and alkaline earth metal salts such as calcium or magnesium salts, and quaternary amine salts of such acid groups, particularly quaternary ammonium salts.

Hydrogel polymers containing organic acid groups that can be reacted with a polyfunctional cross-linking agent useful in the present invention include homopolymers and copolymers of vinylic monomer units, such as homopolymers or copolymers comprising substituted or unsubstituted acrylic acid monomer units or substituted or unsubstituted acrylamide units. Where the hydrogel polymer is a copolymer, at least one of the co-monomer units will contain a functional group, such as an organic acid functional group, that is reactive with a polyfunctional cross-linking agent. Thus, where the functional group in the polymer is an organic acid functional group, any hydrogel polymer prepared, for example, from an ethylenically unsaturated acid, or salt thereof as mentioned above, may be cross-linked with a polyfunctional cross-linking agent and utilized as a coating for a medical device in accordance with the present invention.

Thus, copolymers of, for example, maleic acid, fumaric acid and isocrotonic may be employed, as well as polymers containing substituted or unsubstituted acrylic acid monomer units.

Substituted acrylic acid monomer units include, but are not limited to, those substituted with lower (C1-C6) straight or branched-chain alkyl groups, for example, methacrylic acid. Substituted acrylamide monomer units include, but are not limited to, those substituted with lower straight or branched chain alkyl groups, for example, methacrylamide. Acrylamide monomer units may also be N-substituted with groups including, but not limited to, lower straight or branched chain alkyl substituents. Among presently preferred polymers containing organic acid functional groups are polyacrylic acid and copolymers of acrylic acid and acrylamide monomer units. Other cross-linkable hydrogel polymers include, without limitation, hydrophilic polyurethanes and copolymers of urethane with acrylic monomers such as such as acrylic acid, which may be substituted as described above. Such polymers are disclosed in U.S. Pat. No. 5,702,754.

While the above-mentioned cross-linked hydrogel polymers may be preferred in some embodiments of the invention, it is understood that the present invention should not be construed as limited to any particular type of hydrogel polymer, whether cross-linked or not. Any hydrogel polymer adapted to render an implantable or insertable medical device coated therewith visible under MRI is, therefore, within the scope of the present invention.

When a cross-linked hydrogel polymer is employed, included within the scope of the present invention are those cross-linked hydrogel polymers suitable for coating an implantable or insertable medical device and which can be adapted by varying the degree of cross-linking thereof such that, when coated on an implantable or insertable medical device, the cross-linked hydrogel polymer renders the medical devisable visible under MRI upon insertion or implantation thereof.

Hydrogel polymers that are cross-linked other than by means of reaction of an organic acid functional group in the hydrogel polymer with a polyfunctional cross-linking agent are, therefore, included within the scope of the present invention.

As examples of other cross-linked hydrogel polymers that may be used in accordance with the present invention, are included, without limitation, hydrogel polymers that may be ionically cross-linked. Ionically cross-linked hydrogel polymers for use with implantable or insertable medical devices are disclosed, for example, in U.S. Pat. Nos. 6,096,018 and 6,060,534 each of which is incorporated herein in its entirety by reference. Ionically cross-linked polymers can be either cationic or anionic in nature and include, without limitation, carboxylic, sulfate, and amine functionalized polymers such as polyacrylic acid, polymethacrylic acid, polyhydroxy ethyl methacrylate, polyvinyl alcohol, polyacrylamide, poly(N-vinyl pyrrolidone), polyethylene oxide, hydrolyzed polyacrylonitrile, polyethylene amine, polysaccharides, alginic acid, pectinic acid, carboxy methyl cellulose, hyaluronic acid, heparin, heparin sulfate, chitosan, carboxymethyl chitosan, chitin, carboxymethyl starch, dextran, carboxymethyl dextran, chondroitin sulfate, cationic guar, cationic starch, alginic acid, pectinic acid, pullulan, gellan, xanthan, collagen as well as mixtures, derivatives (such as salts and esters) and copolymers thereof. It is understood that many of these hydrogel polymers may be cross-linked with chemical cross-linking agents and/or with ionic cross-linking agents. Therefore, hydrogel polymers that may be chemically cross-linked do not necessarily form a mutually exclusive group from hydrogel polymers that may be ionically cross-linked. In general, the hydrogel polymers useful in accordance with the present invention can be ionically and/or chemically cross-linked and may be cross-linked by other methods known in the art as well.

The crosslinking ions used to ionically crosslink the hydrogel polymers may be anions or cations depending on whether the polymer is anionically or cationically crosslinkable. Appropriate crosslinking ions include but are not limited to cations selected from the group consisting of calcium, magnesium, barium, strontium, boron, beryllium, aluminum, iron, copper, cobalt, lead and silver ions. Anions may be selected from, but are not limited to, the group consisting of phosphate, citrate, borate, succinate, maleate, adipate and oxalate ions. More broadly, anions are commonly derived from polybasic organic or inorganic acids. Crosslinking may be carried out by methods known in the art, for example, by contacting the polymers with an aqueous solution containing dissolved ions.

As noted above, among various methods of cross-linking hydrogel polymers are included, but not limited to, chemical cross-linking with polyfunctional reagents that bridge hydrogel polymer chains by reaction with functional groups in the hydrogel polymer or cross-linking the hydrogel polymer with polyvalent metal ions. Non-chemical cross-linking methods, such as by exposing the hydrogel polymer to light of an appropriate frequency may also be employed. Chemical cross-linking with polyfunctional reagents is among preferred methods of cross-linking because the degree of crosslinking can often be more readily controlled by, for example, varying the amount and/or type of polyfunctional cross-linking agent employed.

A polyfunctional cross-linking agent can be any compound having at least two sites for reaction with functional groups, such as amide or, in some preferred embodiments, organic acid functional groups, in the hydrogel polymer. Any conventional polyfunctional cross-linking agent known in the art may be employed. Preferably, the crosslinking agent contains one or more of carboxyl, hydroxy, epoxy, halogen or amino functional groups which are capable, via well-known mechanisms such as nucleophilic or condensation reactions, of reacting with functional groups present along the polymer backbone or in the polymer structure. The polyfunctional cross-linking agent may thus comprise, e.g., diazonium, azide isocyanate, acid chloride, acid anhydride, imino carbonate, amino, carboxyl, epoxy, hydroxyl, aldehyde, carbodimide and aziridine groups. Examples of some preferred polyfunctional cross-linking agents include, without limitation, polycarboxylic acids or anhydrides; polyamines; epihalohydrins; diepoxides; dialdehydes such as glutaraldehye; diols; carboxylic acid halides, ketenes and like compounds. Examples of cross-linking agents are found in U.S. Pat. Nos. 5,869,129, 5,702,754 and 6,060,534 each of which is incorporated in its entirety herein by reference. Specific cross-linking agents that may be used include, for example, commercially available preparations sold by Zeneca Resins (e.g., NeoCryl CX 100), preparations sold by EIT Industries (e.g., XAMA-7), and preparations sold by Union Carbide (e.g., Ucarlink XL-29SE). A combination of polyfunctional crosslinking agents may be used to cross-link a hydrogel polymer useful in accordance with the present invention.

The hydrogel polymer, whether cross-linked or not, may be attached to a substrate, i.e., the surface of a medical device, by any means known in the art. The mechanism by which the hydrogel polymer is attached to the surface of the medical device is, therefore, not critical to the practice of the invention disclosed herein. Thus, the hydrogel polymer may be provided on the surface of a substrate by, for example, dipping the medical device, or portion thereof to be coated with the hydrogel polymer, into a solution, dispersion or emulsion of the hydrogel polymer followed by drying to remove the carrier fluid used to dissolve, disperse or emulsify the hydrogel polymer. A solution, dispersion or emulsion of the hydrogel polymer may also be sprayed onto the surface of the medical device followed by drying.

Other methods known in the art for providing a hydrogel polymer coating on the surface of a substrate may also adapted to provide a hydrogel polymer coating on an implantable or insertable medical device in accordance with the present invention. For example, it is also possible to polymerize the hydrogel polymer on the surface of the medical device by contacting the medical device, or portion thereof to be coated with the hydrogel polymer, with a solution, dispersion or emulsion containing a polymerizable monomer or a mixture or polymerizable monomers and any other optional reagents such as cross-linking reagents, initiators, etc., and thereafter causing polymerization to occur in situ on the surface of the medical device. The polymerizable monomer may also be deposited on the surface of the medical device by, for example, plasma enhanced chemical vapor deposition (PECVD) or other methods known in the art. The polymerization reaction occurring on the surface of the medical device may be triggered by, for example, heating the coated medical device or exposing the coated medical device to light of an appropriate frequency. Other methods known in the art for causing polymerization to occur on a substrate may be adapted to provide a hydrogel polymer on the surface of an implantable or insertable medical device in accordance with the present invention.

The surface of the medical device may also be pre-treated or primed to enhance adherence of the hydrogel polymer or a polymerizable monomer to the surface thereof. Such pre-treatment can ultimately result in a hydrogel polymer coating that is more tenaciously adhered to the medical device. In one embodiment, a primer coating is applied to the device surface through conventional methods, including dipping and spraying. The primer solution may comprise, for example, an aqueous solution, dispersion or emulsion of a polymer containing organic acid functional groups and an excess of a polyfunctional cross-linking agent that is reactive with the organic acid groups on the hydrogel polymer, which is subsequently applied to the medical device having the primer coating layer applied thereto. After the primer coat is permitted to dry to form a substantially water-insoluble layer, the dried primer coat is contacted with an aqueous solution, dispersion or emulsion of a hydrogel polymer or hydrogel-forming monomers by conventional methods. The hydrogel polymer may be provided as, for example, an aqueous dispersion or emulsion of a hydrogel polymer or hydrogel-forming monomers, a cross-linking agent and, optionally, a paramagnetic material such as a paramagnetic ion, paramagnetic ion chelation complex or a paramagnetic particle. Alternatively, a paramagnetic material may be loaded into the hydrogel coating after it is applied to the device surface. The hydrogel polymer is bonded to the primer coating layer through excess unreacted polyfunctional cross-linking agent.

One method for attaching the hydrogel polymer to the surface of a medical device that may be advantageously employed in accordance with the present invention is disclosed in U.S. Pat. No. 5,702,752. In this method, the substrate, i.e., the surface of a medical device, is coated with a primer coating composition comprising, for example, an aqueous dispersion or emulsion of a polymer having organic acid functional groups and a polyfunctional crosslinking agent having functional groups capable of reacting with the organic acid functional groups in the subsequently applied hydrogel polymer. The primer coating layer is dried to form a substantially insoluble layer and then the substrate having the primer coating layer disposed thereon is contacted with a solution, dispersion or emulsion of a hydrogel polymer. The polyfunctional crosslinking agent used in this method provides unreacted functional groups for reaction with functional groups, such as organic acid functional groups, in the hydrogel polymer. The functional groups in the polyfunctional cross-linking agent thus serve at least two purposes. The first purpose is to crosslink the primer coating and thereby form a substantially water insoluble primer coating layer. The second purpose is to covalently bond to organic acid groups present in the hydrogel polymer, thereby securing the hydrogel polymer to the primer coating layer. Therefore, sufficient functionality must be present in the crosslinking agent to accomplish both purposes. That is, the amount or type of crosslinking agent used must be sufficient such that enough functional groups are present to substantially crosslink the primer coating and provide unreacted functional groups for covalently bonding to the hydrogel polymer.

Unreacted functional groups in the polyfunctional cross-linking agent may be present, for example, by supplying an excess of the polyfunctional cross-linking agent during application of the primer coating, or by utilizing a polyfunctional cross-linking agent having more than two functional groups per molecule. Among such polyfunctional cross-linking agents having more than two functional groups per molecule are trifunctional aziridines disclosed in U.S. Pat. No. 5,702,754.

The hydrogel polymer may be applied by contacting the first dried cross-linked primer coating layer with an aqueous solution or dispersion of a hydrogel polymer having organic acid functional groups, and drying the combined coating. The hydrogel polymer is thereby bonded to the primer coating by reaction of the organic acid functional groups in the hydrogel polymer with unreacted functional groups in the polyfunctional cross-linking agent. An optional lubricious coating layer may be provided by a similar method. This additional coating layer preferably comprises a hydrogel polymer that provides lubricity that can facilitate insertion of the implantable or medical device into the patient.

The hydrogel polymer, when provided as a coating on a surface of a medical device in accordance with the present invention, will preferably have a thickness in the range of from about 20 to about 3000 microns, more preferably from about 50 to about 2000 microns. Hydrogel polymer thicknesses in the range of from about 100 to about 1000 microns are particularly preferred. The thickness of the hydrogel polymer may be adjusted to enhance the visibility under MRI of the medical device, or a portion thereof, coated with a hydrogel polymer in accordance with the present invention. For example, the medical device may be provided with a substantially uniform thickness of the hydrogel polymer, or selected portions of the medical device may be provided with a thicker or thinner hydrogel polymer coating as desired to enhance contrast with respect to another portion of the medical device. It is understood that the entire surface of the medical device need not be provided with a hydrogel polymer coating in accordance with the present invention. Thus, the coating may be provided only on selected portions of the medical device to enhance the visibility thereof or to render such portions visible under MRI.

In some embodiments of the present invention, the hydrogel polymer is adapted by incorporating a paramagnetic material within the hydrogel polymer such that, when applied as a coating on an implantable or insertable medical device, the medical device is rendered visible under MRI. Paramagnetic materials for use as contrast agents for MRI are known in the art and include, for example, paramagnetic ions, paramagnetic ion chelation complexes, paramagnetic particles and other materials that comprise paramagnetic atoms and enhance the visibility under MRI of detectable species, such as protons. Any paramagnetic material known in the art as an MRI contrast agent may be incorporated within a hydrogel polymer or provided as a coating on an implantable or insertable medical device in accordance with the present invention.

It is believed that the paramagnetic material, when incorporated within a hydrogel polymer coating on a medical device in accordance with the present invention, decreases the spin relaxation time of detectable species such as protons in water or other molecules, compounds or groups associated with the hydrogel polymer. Consequently, the detectable species associated with the hydrogel polymer have enhanced detectability under MRI relative to detectable species in the environment surrounding the medical device. Visibility of the medical device under MRI is, therefore, enhanced.

Among paramagnetic materials that can be incorporated in a hydrogel polymer provided as a coating on a medical device in accordance with the invention include paramagnetic ions and paramagnetic particles. Paramagnetic materials are typically those that have a strong magnetic moment relative to detectable protons in water or other molecules, compounds or groups in the vicinity of the paramagnetic materials. Elements with atomic numbers 21-29, 42, 44, and 58-70, such as chromium (III), manganese (II), iron (III), iron (II), cobalt (II), copper (II), nickel (II), praesodymium (III), neodymium (III), samarium (III), ytterbium (III), gadolinium (III), terbium (III), dysprosium (III), holmium (III) and erbium (III) are examples of paramagnetic elements that can be used in accordance with the present invention. A widely used element in paramagnetic materials for MRI contrast agents is gadolinium (III), a lanthanide having seven unpaired electrons in the 4f orbital, which has a large magnetic moment. The large magnetic moment of the gadolinium (III) causes a localized reduction of the relaxation times in the protons in its environment, resulting in enhanced visibility of the magnetic resonance images. Paramagnetic materials based on gadolinium (III) are, therefore, among preferred paramagnetic materials that can be incorporated within a hydrogel polymer coating on an implantable or insertable medical device in accordance with the present invention.

Paramagnetic material can be incorporated within the hydrogel polymer by, for example, contacting the medical device having the hydrogel polymer coated thereon with the paramagnetic material, e.g., a solution of a soluble salt of the paramagnetic ion, or a solution comprising a paramagnetic ion chelation complex. Alternatively, the paramagnetic material can be incorporated within the hydrogel polymer by, for example, contacting the hydrogel polymer or a monomer precursor thereof with the paramagnetic ions or a chelation complex thereof prior to formation of the hydrogel polymer coating on the surface of the implantable or insertable medical device. The paramagnetic ion or chelation complex thereof then becomes incorporated within the hydrogel polymer matrix, for example, by absorption/entrapment within the hydrogel polymer matrix and/or adsorption on the surface of the hydrogel polymer.

Where paramagnetic ions are incorporated, it is particularly advantageous if the hydrogel polymer comprises groups that facilitate securing the paramagnetic ions onto and/or within the hydrogel polymer. Such groups may, for example, comprise organic acid functional groups or other anionically ionizable groups in or covalently bonded to the hydrogel polymer. It is believed that the electrostatic attraction or ionic bonding of the cationic paramagnetic ions to anionic groups such as carboxyl or other groups in or covalently bonded to the hydrogel polymer (e.g., pendant from the hydrogel polymer backbone) can secure the paramagnetic ions within and/or onto the hydrogel polymer. The anionically ionizable groups may also be functionally referred to herein as paramagnetic ion chelating groups. The paramagnetic ions are, therefore, held by the hydrogel polymer such that excessive leaching of such ions is prevented. Substantial immobilization of the paramagnetic ions within the hydrogel polymer is, of course, important to ensure that the hydrogel coating, and hence medical device coated therewith, will have maximum visibility and durability under MRI. Moreover, the paramagnetic ions are often toxic and can, therefore, produce adverse reactions if excessively leached from the coating and thereafter distributed systemically or absorbed in specific areas of the patient.

Hence, hydrogel polymers that comprise paramagnetic ion chelating groups are also useful in the present invention. Such paramagnetic ion chelating groups can be covalently bonded to the hydrogel polymer by, for example, reacting a polymerizable olefinic monomer containing a paramagnetic ion chelating functionality with a hydrophilic monomer such as substituted or unsubstituted acrylic acid or acrylamide. The paramagnetic chelating functionality can be provided, for example, by utilizing a polymerizable monomer containing an aminopolycarboxylic acid group. Among aminopolycarboxylic acid groups or other metal chelating groups that may be incorporated within a polymerizable monomer used for forming a hydrogel, or otherwise incorporated within a hydrogel polymer in accordance with the present invention, are those known in the art for chelating metal ions and include, without limitation, diethylene triaminepentaacetic acid (DTPA); 1,4,7,10-tetraazacyclododecane-N,N,N',N'''-tetraacetic acid (DOTA); ethylenediaminetetraacetic acid (EDTA); 1,4,7,10-tetraazacyclododecane-N,N',N''-triacetic acid (DO3A); 1,4,7-triazacyclononane-N,N',N''-triacetic acid (NOTA); 1,4,8,11-tetraazacyclotetradecane-N,N',N'', N'''-tetraacetic acid (TETA); and hydroxybenzylethylene-diamine diacetic acid (HBED). The paramagnetic ions may be incorporated within the hydrogel polymer for chelation with such metal chelating groups before or after the hydrogel polymer is provided on the surface of the implantable or insertable medical device.

The hydrogel polymer used to coat medical devices in accordance with the present invention may also comprise a paramagnetic ion chelation complex that is not necessarily covalently bonded to the hydrogel polymer. Such paramagnetic chelation complexes may, for example, be complexes of any paramagnetic ion, such as those mentioned hereinabove, with any conventional metal chelating compound including, without limitation, DTPA, DOTA, EDTA, NOTA, TETA and HBED. Gadolinium diethylene triaminepentaacetic acid (Gd-DTPA) is among presently preferred paramagnetic ion chelation complexes that can be incorporated in a hydrogel polymer for coating a medical device in accordance with the present invention. A paramagnetic ion chelation complex can be incorporated within the hydrogel polymer by contacting the hydrogel polymer with, e.g., a solution of the chelation complex, either before or after the hydrogel polymer is formed on the surface of an implantable or insertable medical device. For example, the chelating compound can be incorporated within a hydrogel polymer by, for example, forming a suspension or dispersion of the hydrogel and chelating compound and, thereafter applying the suspension or dispersion to the surface of a medical device, followed by drying.

The chelating compound can also be combined with the hydrogel-forming monomers, and any crosslinking agents used to form the hydrogel polymer, prior to polymerizing the same. It is also possible to apply the chelating compound to the surface of a medical device previously coated with a hydrogel polymer by, e.g., by spraying a solution of the chelating compound on the polymer, or dipping the polymer into the same.

The hydrogel polymer used in an implantable or insertable medical device in accordance with the present invention may also have incorporated therein paramagnetic particles. Paramagnetic particles are distinguished herein from paramagnetic ions or chelation complexes of paramagnetic ions in that such particles, as the name implies, are solids. Such solids are, preferably, substantially insoluble in an aqueous environment, such as the aqueous environment of a hydrogel having water associated therewith or the aqueous environment provided by bodily fluids in contact with the implantable or insertable medical device coated with a hydrogel polymer.

Such paramagnetic particles can be incorporated within a hydrogel polymer by, for example, forming a suspension or dispersion of the hydrogel and paramagnetic particles and, thereafter applying the suspension or dispersion to the surface of a medical device, followed by drying. The paramagnetic particles can also be combined with the hydrogel-forming monomers, and any crosslinking agents used to form the hydrogel polymer, prior to polymerizing the same. It is also possible to apply the paramagnetic particles to the surface of a medical device previously coated with a hydrogel polymer by, e.g. contacting the coated medical device with the particles by spraying the particles onto the coated medical device. Other methods known in the art for coating polymeric surfaces with particulate substances may also be adapted to provide a hydrogel coated medical device in accordance with the present invention wherein a surface thereof comprises paramagnetic particles.

Any paramagnetic particles known in the art for use as MRI contrast agents may be utilized in this embodiment of the present invention. Among such paramagnetic particles that are useful, therefore, include solid compounds of any of the paramagnetic elements mentioned above. Particularly preferred solid compounds of such elements include the paramagnetic and superparamagnetic oxides of such elements. Among presently preferred paramagnetic particles are ultrasmall superparamagnetic iron oxide particles coated with starch or other polysaccharides or cellulosic materials. Examples of such coated ultrasmall iron oxide particles are found, for example, in U.S. Pat. Nos. 6,207,134 and 6,123,920 (and the patents cited therein) assigned to Nycomed Imaging AS, both of which are incorporated in their entireties herein by reference.

In embodiments of the present invention wherein any of the above-described or other paramagnetic materials are incorporated within a hydrogel polymer, it may be preferred to utilize a cross-linked hydrogel polymer. In addition to the previously mentioned advantages of using cross-linked hydrogel polymers for medical devices in accordance with the present invention, such polymers can also facilitate immobilization of the paramagnetic materials incorporated therein. Paramagnetic ions or other paramagnetic materials are more effectively immobilized within the matrix provided by a cross-linked hydrogel polymer and are, thereby, less susceptible to leaching from the hydrogel polymer. In addition, immobilization of the paramagnetic ions incorporated within a cross-linked hydrogel may be further enhanced by ionic bonding of the paramagnetic ions to, for example, organic acid functionality or metal chelating functionality provided by the hydrogel polymer as described above. Further, where the hydrogel polymer is cross-linked, metal chelating functionality can also be provided by utilizing a polyfunctional cross-linking agent that comprises a metal chelating group covalently bonded to the cross-linking agent. Any metal chelating group including, without limitation, DTPA, DOTA, EDTA, NOTA, TETA and HBED, that can be covalently bonded to a functional group in a cross-linking agent, while retaining the ability of the cross-linking agent to cross-link the hydrogel polymer is within the scope of the present invention. Further, polyfunctional cross-linking agents having, for example, groups such as carboxyl groups that facilitate electrostatic attraction or ionic bonding thereto of paramagnetic cations are within the scope of the present invention. Chelation of paramagnetic ions to metal chelating groups covalently bonded to the cross-linking agent or electrostatic attraction/ionic bonding of paramagnetic ions to groups in the cross-linking agent may further enhance the ability of the cross-linked hydrogel polymer to immobilize the paramagnetic ions.

The present invention is also directed to the use of an implantable or insertable medical device of the present invention in a medical procedure, wherein during or after insertion or implantation of the medical device in a patient, the position of the medical device is viewed under magnetic resonance imaging. The medical device, as described hereinabove, comprises (a) a substrate and (b) a hydrogel polymer coating at a least a portion of the surface of the substrate, wherein the hydrogel polymer is adapted to render the medical device visible under magnetic resonance imaging upon insertion or implantation of the medical device into a patient.

In another embodiment, the present invention is directed to the use of a hydrogel polymer for coating at least a portion of the surface of a medical device, wherein the hydrogel polymer is adapted to render the medical device coated with the hydrogel polymer visible under magnetic resonance imaging during or after insertion or implantation of the medical device in a patient. The hydrogel polymer can be any hydrogel polymer described herein that is adapted for rendering the medical device visible under magnetic resonance imaging.

The present invention is also directed to a hydrogel polymer adapted to render a medical device coated with the hydrogel polymer visible under magnetic resonance imaging during or after insertion of the medical device in a patient. The hydrogel polymer can be any hydrogel polymer described herein that is adapted for rendering the medical device visible under magnetic resonance imaging.

The present invention is not limited in scope to any particular implantable or insertable medical device or any material used to form such medical device. Therefore, the present invention has wide applicability to all types of implantable or insertable medical devices known in the art whether such medical devices are used primarily in conjunction with observational, diagnostic or therapeutic medical procedures. Most generally, the present invention may be practiced with any implantable or insertable medical device for which visualization thereof under MRI during or after insertion of the device is desired.

Among such implantable or insertable medical devices are included, without limitation, catheters such as neuro-interventional microcatheters; guide wires; balloons such as those used in angioplasty procedures; stents including endovascular, biliary, tracheal, gastrointestinal, urethral, ureteral and esophageal stents; stent grafts; prosthetic devices such as artificial limbs; endoscopic devices; and, laparoscopic devices. The medical device comprising the substrate onto which the hydrogel polymer is coated in accordance with the present invention can be constructed of any material conventionally used for such devices including, without limitation, metals and metal alloys such as superelastic shape memory alloys; ceramics; glasses; polymeric materials which may be based on natural, semi-synthetic, and synthetic polymeric materials; and composites of any of such materials. The material is preferably a biocompatible material, i.e., does not produce, either systemically or locally, an unacceptable adverse reaction in the patient, and may be biodegradable or substantially non-biodegradable in the environment surrounding the medical device upon insertion or implantation thereof. Biocompatibility of the material used to construct the medical device may be enhanced by providing a biocompatible hydrogel coating in accordance with the present invention.

The hydrogel polymer coating the medical device in accordance with the present invention can also be adapted to incorporate a diagnostic or a therapeutic agent such as a drug. Incorporation of a therapeutic agent in a coating provided on the surface of a medical device is generally known in the art and is advantageous inter alia, because it enables localized administration of the therapeutic agent. Localized administration is, in many cases, beneficial to ensure that a therapeutically effective amount of the agent is administered to the target location and to minimize adverse reactions associated with systemic administration of the agent. Any methods known in the art for loading a therapeutic agent within or on the surface of a polymeric material to be provided as a coating on a medical device can be employed. In the context of the present invention, the therapeutic agent can be included within a solution, dispersion or emulsion of the hydrogel polymer or hydrogel-forming monomers to be provided as a coating onto the medical device. Alternatively, the therapeutic agent can be incorporated into a hydrogel coating previously applied onto the medical device by, for example, dipping or soaking the medical device in a solution or dispersion of the therapeutic agent followed by drying, or by spraying a solution or dispersion of the therapeutic agent onto the medical device coated with the hydrogel polymer.

EXAMPLES

In order to characterize the ability of the hydrogel to retain the paramagnetic ions, loading and release tests were performed on a coated substrate. A portion of coated substrate was soaked and shaken in a vial at 37° C. Aliquots of the soaking solution were removed at certain time points and the amount of paramagnetic ion was measured by an appropriate technique, e.g., the amount of gadolinium (III) was measured using Inductively Coupled Plasma-Atomic Emission Spectroscopy (ICP-AES), monitoring at 342.247 nm (nanometers).

The results demonstrate that the amount of gadolinium released over time did not vary significantly, e.g., 7.4 micrograms (µg)/inch of catheter after 1 minute of soaking compared to 9.8 µg/inch of catheter after 4 hours of soaking. In addition, by weighing the coated substrates loaded with the paramagnetic ion complex, and comparing the weights against controls where no paramagnetic ion was added to the hydrogel solutions, the amount of paramagnetic ion present on the substrate could be estimated. Therefore, the percent of paramagnetic ion released was also calculated. The data indicated that the majority of gadolinium is retained in the hydrogel without leaching out during prolonged soaking of the coated substrate. For example, 96.5% of the gadolinium was retained after 1 minute of soaking and 95.4% of the gadolinium was retained after 4 hours of soaking.

The durability of the hydrogel coating is also an important consideration. Durability of the coating ensures prolonged visibility of the device since its MR image will fade away or completely disappear if the coating breaks down and the paramagnetic ions cannot be retained near the surface of the device. In order to test the durability of the coating, the coated substrates were pre-soaked in saline for certain periods of time before being placed in another medium and visualized by MRI. Uncoated substrate was used as a control. In contrast to the control samples, all of the coated substrates were visible by MRI after 0, 5, 10, 20, 40, and 60 minutes of soaking in a saline solution.

The following are example methods of preparing and testing various primer solutions and hydrogels. These examples should not be construed as limiting the scope of the invention in any manner.

Example 1

Preparation of Primer Solutions

Primer 1
In a glass beaker, 980 grams of Bayhydrol PR240, available through Bayer, and 20 grams of NeoCryl CX-100, available through NeoResin, were stirred until thoroughly mixed. Bayhydrol PR240 is a solvent-free anionic aliphatic polyurethane dispersion in water. NeoCryl CX-100 is a polyfunctional aziridine crosslinking agent.

Primer 2
In a glass beaker, 875 grams of Bayhydrol PR240, 25 grams of NeoCryl CX-100, and 100 grams of D.I. water were stirred until thoroughly mixed.

Example 2

Preparation of Hydrogel Containing Paramagnetic Ions

Hydrogel 1
990 grams of deionized water was poured into a glass beaker and the mixer was started. 10 grams of Glascol WN33, by Allied Colloids, a copolymer of sodium acrylate and acrylamide, was slowly added into the beaker. The beaker was covered with parafilm and the solution was stirred continuously for 15 hours until the Glascol WN33 had sufficiently dissolved to obtain a 1% (wt) Glascol solution. 13.5 grams of Gd-DTPA, by Aldrich, was then added into the Glascol WN33 solution very slowly, with stirring, in order to avoid forming any precipitate. Gd-DTPA (diethylenetriaminepentaacetic acid, gadolinium(III) dihydrogen salt hydrate) is a stable Gd(III) chelate widely used as MRI contrast agent. A proper amount of ammonium hydroxide was added to adjust to pH 8-10. The beaker was then covered with parafilm and the solution was continuously stirred for 6-15 hours until the Glascol WN33 and Gd-DTPA were thoroughly mixed and dissolved. 3.8 grams of 23% (wt) sodium chloride solution was added with stirring. Preparation was complete after 40 grams of Primer 1 fluid was added and thoroughly mixed.

Hydrogel 2
950 grams of de-ionized water was poured into a glass beaker and the mixer was started. 40 grams of Glascol S19, by Allied Colloids, polyacrylic acid, was slowly added into the beaker. The beaker was covered with parafilm and the solution was stirred continuously for 15 hours until the Glascol S19 had sufficiently dissolved to obtain a 1% (wt) Glascol solution. 10 grams of Gd-DTPA, by Aldrich, was then added into the Glascol S19 solution very slowly with stirring in order to avoid forming any precipitate. The beaker was then covered with parafilm and the solution was continuously stirred for 6-15 hours until the Glascol S19 and Gd-DTPA were thoroughly mixed and dissolved. 5.0 grams of 23% (wt) sodium chloride solution was added, followed by a proper amount of ammonium hydroxide to adjust to pH 9-10. Preparation was complete after 40 grams of Primer 1 fluid was added and thoroughly mixed.

Hydrogel 3

975 grams of deionized water was poured into a glass beaker and the mixer was started. 15 grams of Glascol WN23, by Allied Colloids, a copolymer of acrylic acid and acrylamide, was slowly added into the beaker. The beaker was covered with parafilm and the solution was stirred continuously for 15 hours until the Glascol WN23 had sufficiently dissolved to obtain a 1% (wt) Glascol solution. 10 grams of Gd-DTPA, by Aldrich, was then added into the Glascol WN23 solution very slowly, with stirring, in order to avoid forming any precipitate. The beaker was then covered with parafilm and the solution was continuously stirred for 6-15 hours until the Glascol WN23 and Gd-DTPA were thoroughly mixed and dissolved. 5.0 grams of 23% (wt) sodium chloride solution was added with stirring, followed by a proper amount of ammonium hydroxide to adjust to pH 9-10. 20 grams of Primer 1 fluid was then added and the solution was thoroughly mixed. Preparation was complete after 5 grams of NeoCryl CX-100 was added drop-wise with agitation.

Hydrogel 4

700 grams of de-ionized water was poured into a glass beaker and the mixer was started. 300 grams of Glascol E15, by Allied Colloids, an aqueous polyacrylic acid solution with 15% solid content, was slowly added into the beaker. The beaker was covered with parafilm and the solution was stirred continuously for 15 hours until the Glascol E15 had sufficiently dissolved to obtain a 1% (wt) Glascol solution. 10 grams of Gd-DTPA, by Aldrich, was then added into the Glascol E15 solution very slowly, with stirring, in order to avoid forming any precipitate. The beaker was then covered with parafilm and the solution was continuously stirred for 6-15 hours until the Glascol E15 and Gd-DTPA were thoroughly mixed and dissolved. 5.0 grams of 23% (wt) sodium chloride solution was added with stirring, followed by a proper amount of ammonium hydroxide to adjust to pH 9-10. Preparation was complete after 10 grams of NeoCryl CX-100 was added drop-wise with agitation.

Example 3

Immobilization of Hydrogel Containing Paramagnetic Ions

Hydrogel 1

A 6 French (F) catheter made of polyether-amide was cleaned with isopropanol. A Teflon coated stainless steel mandrel of proper size was inserted into the lumen to keep the catheter straight. The catheter was immersed in the Primer 1 solution and dried in the open air for 10 minutes. The catheter was then immersed into the Hydrogel 1 solution and dried in the open air for 15 minutes. The catheter was then immersed again into the Hydrogel 1 solution, air-dried for 15 minutes and then placed in an oven at 140° F. for post curing for 8-24 hours.

Hydrogel 2

A 3 French catheter made of polyethylene was cleaned with isopropanol. A Teflon coated stainless steel mandrel of proper size was inserted into the lumen to keep the catheter straight. The catheter was immersed in the Primer 1 solution and dried in the open air for 10 minutes. The catheter was then immersed in the Hydrogel 2 solution and subsequently air-dried for 15 minutes. The step of immersing the catheter in the Hydrogel 2 solution, followed by air-drying, was repeated before it was placed in an oven at 140° F. for post curing for 8-24 hours.

Hydrogel 3

A 3 French catheter made of nylon was cleaned with isopropanol. A Teflon coated stainless steel mandrel with proper size was inserted into the lumen to keep the catheter straight. The catheter was immersed in the Primer 2 solution, and subsequently dried in the open air for 10 minutes. The catheter was then immersed in the Hydrogel 3 solution, followed by air-drying for 15 minutes. The step of immersing the catheter in the Hydrogel 3 solution, followed by air-drying, was repeated before the catheter was placed in an oven at 140° F. for post curing for 8-24 hours.

Hydrogel 4

A 6 French catheter made of polyurethane was cleaned with isopropanol. A Teflon coated stainless steel mandrel of proper size was inserted into the lumen to keep the catheter straight. The catheter was immersed in the Primer 1 solution and then dried in the open air for 10 minutes. The catheter was then dipped into the Hydrogel 4 solution and subsequently air-dried for 15 minutes. The step of immersing the catheter in the Hydrogel 4 solution, followed by air-drying, was repeated before the catheter was placed in an oven at 140° F. for post curing for 8-24 hours.

Example 4

Loading and Release Tests of Paramagnetic Ions

A piece of a 6 French polyether-amide catheter coated with Hydrogel 1, approximately an inch in length, was cut and placed in a 5 ml polypropylene vial. After adding 5.0 ml of a phosphate buffered solution ("PBS") in the vial to soak the catheter, the vial was placed on a shaker in the oven at 37° C. After soaking for 1 minute, 5 minutes, 30 minutes, 1 hour, and 4 hours, an aliquot of the soaking solution was taken to determine the amount of gadolinium present by ICP-AES, monitored at 342.247 nm. The amount of gadolinium released from the coated catheter, in µg/inch, was calculated and is shown in Table I below.

The percent of gadolinium released was also estimated and is shown in Table The substrates were weighed after immersing only in the primer solution, immersing once in the hydrogel solution, and immersing twice in the hydrogel solution. The differences in weight of the coated substrates were calculated, yielding the amount of Glascol and Gd-DTPA coated on each substrate. A control was run in which the hydrogel solutions did not contain any Gd-DTPA. Therefore, the amount of gadolinium on the substrate could be estimated by comparing the weights of the substrates with and without the Gd-DTPA, and the percentage of gadolinium released from the coat could be calculated.

TABLE 1

Soaking test of the coated catheter in PBS solution

| | Time of soaking in PBS solution | | | | |
|---|---|---|---|---|---|
| | 1 min | 5 min | 30 min | 1 hr | 4 hrs |
| Released Gd (μg/inch coated catheter) | 7.4 | 7.0 | 9.4 | 9.8 | 9.8 |
| % of Gd Released | 3.5 | 3.3 | 4.4 | 4.6 | 4.6 |

Example 5

MRI Images of the Hydrogel Containing Paramagnetic Ions

The hydrogel samples coated in Example 3 were tested in phantom under MRI to determine their visibility over time. In order to check the durability of the gadolinium visibility in the hydrogel, the samples coated with the different hydrogels were pre-soaked in saline for certain amounts of time before they were placed in fat-free yogurt phantom, a tissue mimic, and viewed by MRI. The soaking times were 0, 5, 10, 20, 40, and 60 minutes. An uncoated 6 French nylon catheter was used as a control. All of the coated samples were visible at every time point analyzed. The control sample was not visible at any of the time points. This is summarized in Table 2 below.

TABLE 2

MRI Visibility Summary of Samples

| Samples | 0 min | 5 min | 10 min | 20 min | 40 min | 60 min |
|---|---|---|---|---|---|---|
| Uncoated | ○ | ○ | ○ | ○ | ○ | ○ |
| Hydrogel 1 | X | X | X | X | X | X |
| Hydrogel 2 | X | X | X | X | X | X |
| Hydrogel 3 | X | X | X | X | X | X |

○: not visible;
X: visible

The following MRI scan parameters were used with a Siemens 1.0T Harmony MRI scanner: the Pulse Sequence was set to SE__14b89; TR=400 ms; TE=15 ms; coronal and axial images FOV=200 mm; 90° flip angle; 10 slices; number of acquisitions=2 (total imaging time=3 min 28 seconds); distance factor=0.3 (separation between slices is 1.3×slice thickness); slice thickness=2.0 mm; in-plane resolution=0.78 mm×0.78 mm; matrix=256×256.

Example 6

Effect of Degree of Hydrogel Polymer Cross-linking on Proton Relaxation Time

The effect of varying the degree of cross-linking on the relaxation time of protons associated with a hydrogel polymer was determined. Three aqueous solutions of Glascol WN33 (0.5 wt %) were prepared in beakers. The first solution contained no cross-linking agent; the second solution contained 0.1 wt % CX-100 as a cross-linking agent; and, the third solution contained 0.25% wt % CX-100. The beakers containing the solutions were subjected to MRI wherein the time between successive excitation pulses was 150, 200, 300, 400, 600 and 1000 milliseconds (ms). The proton T1 (longitudinal spin) relaxation time was calculated, based on the observed signal intensity, for each of the three solutions at the successive excitation pulses as is known in the art. T1 for solution 1 was 5356 ms; T1 for solution 2 was 5524 ms; and, T2 for solution 3 was 4690 ms. These results demonstrate that a hydrogel polymer can be adapted by cross-linking to varying degrees to the modify relaxation time of detectable protons associated with the hydrogel polymer.

What is claimed is:

1. A method of enhancing the visibility of an insertable or implantable medical device under MRI, the medical device comprising a coating, the coating consists of a crosslinked hydrogel polymer and a compound comprising hydroxyl groups, the compound comprising hydroxyl groups is glycerin, the visibility of the medical device is enhanced under MRI by altering the magnetic properties of detectable protons associated with the device relative to detectable protons in the surrounding environment cross-linking of the cross-linked hydrogel polymer to varying degrees on at least a portion of said device, the medical device is inserted and/or implanted in a body lumen, the position of the medical device is determined by distinguishing the detectable protons associated with the device relative to the detectable protons in the surrounding environment with MRI.

2. The method of claim 1, wherein said hydrogel polymer is altered by decreasing the relaxation time of said detectable protons associated with said hydrogel polymer relative to the relaxation time of said detectable protons in the environment surrounding the device.

3. The method of claim 2, wherein water molecules associated with said hydrogel polymer comprise said detectable protons.

4. The method of claim 3, wherein hydroxyl groups associated with said hydrogel polymer comprise said detectable protons.

5. The method of claim 4, wherein a compound dispersed within said hydrogel polymer comprises said hydroxyl groups.

6. The method of claim 1, wherein said cross-linked hydrogel polymer is further adapted by incorporating paramagnetic ions in said hydrogel polymer.

7. The method of claim 6 wherein said cross-linked hydrogel polymer comprises paramagnetic ion chelating groups.

8. The method claim 7, wherein said paramagnetic ion chelating groups are covalently bonded to the cross-linked hydrogel polymer.

9. The method of claim 7, wherein said paramagnetic ion chelating groups comprise organic acid functional groups.

10. The method of claim 9, wherein said paramagnetic ion chelating groups comprise carboxyl groups.

11. The method of claim 10, wherein said cross-linked hydrogel polymer comprises substituted or unsubstituted acrylic acid groups.

12. The method of claim 11, wherein said cross-linked hydrogel polymer comprises polyacrylic acid.

13. The method of claim 11, wherein said cross-linked hydrogel polymer further comprises substituted or unsubstituted acrylamide monomer units.

14. The method claim 13, wherein said hydrogel polymer is a copolymer of acrylic acid and acrylamide.

15. The method of claim 7, wherein said paramagnetic ion chelating groups comprise aminopolycarboxylic acid groups.

16. The method of claim 6, wherein said cross-linked hydrogel polymer comprises a paramagnetic ion chelation complex.

17. The method of claim 16, wherein said paramagnetic ion chelation complex is covalently bonded to said cross-linked hydrogel polymer.

18. The method of claim 16, wherein said paramagnetic ion chelation complex is selected from the group consisting of diethylene triamine pentaacetic acid (DTPA), tetraazacyclododecane tetraacetic acid (DOTA), and tetraazacyclo tetradecane tetraacetic acid (TETA).

19. The method of claim 18, wherein said paramagnetic chelation complex comprises diethylenetriamine pentaacetic acid (DTPA).

20. The method of claim 6, wherein said paramagnetic ions are selected from the group of chromium (III), manganese (II), iron (III), iron (II), cobalt (II), copper (II), nickel (II), praesodymium (III), neodymium (III), samarium (III), ytterbium (III), gadolinium (III), terbium (III), dysprosium (III), holmium (III) and erbium (III).

21. The method of claim 20, wherein said paramagnetic ions comprise gadolinium (III).

22. The method of claim 1, wherein said cross-linked hydrogel polymer is further adapted by incorporating paramagnetic particles in said hydrogel polymer.

23. The method of claim 22, wherein said paramagnetic particles comprise starch-coated iron oxide particles.

24. The method of claim 1, wherein said cross-linked hydrogel polymer is selected from the group consisting of cross-linked polyacrylates; poly(acrylic acid); poly(methacrylic acid); polyacrylamides; poly(N-alkylacrylamides); polyalkylene oxides; poly(ethylene oxide); poly(propylene) oxide; poly(vinyl alcohol); polyvinyl aromatics; poly(vinylpyrrolidone); poly(ethyleneimine); polyethylene amine; polyacrylonitrile; polyvinyl sulfonic acid; polyamides; poly (L-lysine); hydrophilic polyurethanes; maleic anhydride polymers; proteins; collagen; cellulosic polymers; methyl cellulose; carboxymethyl cellulose; dextran; carboxymethyl dextran; modified dextran; alginates; alginic acid; pectinic acid; hyaluronic acid; chitin; pullulan; gelatin; gellan; xanthan; carboxymethyl starch; chondroitin sulfate; guar; starch; and copolymers, mixtures and derivatives thereof.

25. The method of claim 1, wherein said cross-linked hydrogel polymer is selected from the group consisting of cross-linked poly(acrylic acid); polyacrylamide; poly(N-alkylacrylamide); copolymers of acrylic acid and acrylamide; poly(ethylene oxide); poly(propylene oxide); copolymers of ethylene oxide and propylene oxide; hyaluronic acid; and poly(L-lysine).

26. The method of claim 1, further comprising disposing a lubricious coating layer on said cross-linked hydrogel polymer.

27. The method of claim 1, wherein said medical device is selected from the group consisting of catheters, guide wires, balloons and stents.

28. The method of claim 27, wherein said catheter is a neuro-interventional microcatheter.

29. The method of claim 27, wherein the stent is selected from the group consisting of endovascular, biliary, tracheal, gastrointestinal, urethral, ureteral and esophageal stents.

30. The method of claim 29, wherein the stent is a coronary stent.

31. The method of claim 1 further comprising disposing an adherence enhancing primer coating under said cross-linked hydrogel polymer.

32. The method of claim 1, comprising forming a first cross-linked hydrogel polymer coating from a first solution having a first cross-linking agent concentration, and forming a second cross-linked hydrogel polymer coating from a second solution having a second cross-linking agent concentration that differs from the first cross-linking agent concentration, and subjecting said first and second cross-linked hydrogel polymer coatings to MRI.

33. The method of claim 1 wherein said detectable protons are associated with a compound other than water molecules.

* * * * *